United States Patent
Popovic et al.

(10) Patent No.: US 9,878,153 B2
(45) Date of Patent: Jan. 30, 2018

(54) APPARATUS FOR EXTERNAL ACTIVATION OF PARALYZED BODY PARTS BY STIMULATION OF PERIPHERAL NERVES

(75) Inventors: Dejan Popovic, San Sebastian (ES); Nebojša Malešević, San Sebastian (ES); Thierry Keller, San Sebastian (ES)

(73) Assignee: FUNDACION TECNALIA RESEARCH & INNOVATION, Donostia-San Sebastian (ES)

(*) Notice: Subject to any disclaimer, the term of this patent is extended or adjusted under 35 U.S.C. 154(b) by 167 days.

(21) Appl. No.: 13/519,239

(22) PCT Filed: Dec. 30, 2009

(86) PCT No.: PCT/EP2009/068023
§ 371 (c)(1),
(2), (4) Date: Aug. 17, 2012

(87) PCT Pub. No.: WO2011/079866
PCT Pub. Date: Jul. 7, 2011

(65) Prior Publication Data
US 2012/0310303 A1    Dec. 6, 2012

(51) Int. Cl.
*A61N 1/36* (2006.01)
*A61N 1/04* (2006.01)
*A61N 1/22* (2006.01)
*A61N 1/32* (2006.01)

(52) U.S. Cl.
CPC ....... *A61N 1/36003* (2013.01); *A61N 1/0456* (2013.01); *A61N 1/0476* (2013.01); *A61N 1/0484* (2013.01); *A61N 1/0492* (2013.01); *A61N 1/36014* (2013.01); *A61H 2201/10* (2013.01); *A61H 2201/165* (2013.01); *A61H 2201/501* (2013.01); *A61H 2201/5035* (2013.01); *A61H 2201/5046* (2013.01); *A61H 2201/5061* (2013.01);
(Continued)

(58) Field of Classification Search
CPC ............ A61N 1/36003; A61N 1/36007; A61N 1/36014
USPC .............................................. 607/48, 49, 115
See application file for complete search history.

(56) References Cited

U.S. PATENT DOCUMENTS

| 710,429 A | 10/1902 | Collins |
| 4,556,214 A * | 12/1985 | Petrofsky et al. ................ 482/1 |
| 4,586,495 A * | 5/1986 | Petrofsky ......................... 602/2 |

(Continued)

FOREIGN PATENT DOCUMENTS

EP    1 610 677 B1    11/2007

OTHER PUBLICATIONS

Bajd, T. et al., "Functional Electrical Stimulation with Surface Electrodes", Journal of Automatic Control, University of Belgrade, 2008, vol. 18, No. 2, pp. 3-9.
(Continued)

*Primary Examiner* — Michael D Abreu
(74) *Attorney, Agent, or Firm* — Florek & Endres PLLC (57) ABSTRACT

Apparatus for external activation of paralyzed body parts by stimulation of peripheral nerves which comprises a soft apparel provided with multi-pad electrodes on one side and activating means on the other side, wherein the activating means are adapted to allow activation and control of a delivered electrical pulse to each multi-pad electrode separately.

7 Claims, 11 Drawing Sheets

(52) U.S. Cl.
CPC ............... *A61H 2201/5071* (2013.01); *A61H 2201/5084* (2013.01); *A61N 1/22* (2013.01); *A61N 1/321* (2013.01)

(56) References Cited

U.S. PATENT DOCUMENTS

| | | | |
|---|---|---|---|
| 4,586,510 A * | 5/1986 | Glaser et al. | 607/48 |
| 4,642,769 A * | 2/1987 | Petrofsky | 607/48 |
| 5,081,989 A | 1/1992 | Graupe | |
| 5,330,516 A * | 7/1994 | Nathan | 607/48 |
| 5,628,722 A * | 5/1997 | Solomonow et al. | 602/26 |
| 5,957,812 A * | 9/1999 | Harrigan | 482/8 |
| 6,066,075 A * | 5/2000 | Poulton | 482/8 |
| 6,341,237 B1 * | 1/2002 | Hurtado | 607/148 |
| 7,072,721 B1 | 7/2006 | Trent | |
| 2004/0023759 A1 | 2/2004 | Duncan et al. | 482/57 |
| 2005/0209049 A1 * | 9/2005 | Shields | 482/8 |
| 2006/0085047 A1 | 4/2006 | Unsworth | |
| 2006/0229160 A1 * | 10/2006 | Talluri | 482/1 |
| 2007/0249466 A1 * | 10/2007 | Chiari et al. | 482/1 |
| 2009/0018612 A1 * | 1/2009 | Duncan et al. | 607/48 |
| 2010/0004715 A1 * | 1/2010 | Fahey | 607/48 |

OTHER PUBLICATIONS

Berkelmanns, R., "FES Cycling", Journal of Automatic Control, University of Belgrade, 2008, vol. 18, No. 2, pp. 73-76.

Broderick, B.J. et al., "Electronic Stimulators for Surface Neural Prosthesis", Journal of Automatic Control, University of Belgrade, 2008, vol. 18, No. 2, pp. 25-33.

Davoodi, R., "Rowing with FES", Journal of Automatic Control, University of Belgrade, 2008, vol. 18, No. 2, pp. 77-84.

Gollee, H. et al., "Abdominal stimulation for respiratory support in tetraplegia: a tutorial review", Journal of Automatic Control, University of Belgrade, 2008, vol. 18, No. 2, pp. 85-92.

Keller, T. and Kuhn, A., "Electrodes for transcutaenous (surface) electrical stimulation", Journal of Automatic Control, University of Belgrade, 2008, vol. 18, No. 2, pp. 35-45.

Miler, V. et al., "Neural Prosthesis for the Therapy of Low Back Pain", Journal of Automatic Control, University of Belgrade, 2008, vol. 18, No. 2, pp. 93-97.

Miller, R.C. et al., "Functional Electrical Stimulation Therapy Improves Grasping in Chronic Cervical Spinal Cord Injury: Two Case Studies", Journal of Automatic Control, University of Belgrade, 2008, vol. 18, No. 2, pp. 53-61.

Popović, D.B. and Sinkjær, T., "Central nervous System Lesions Leading to Disability", Journal of Automatic Control, University of Belgrade, 2008, vol. 18, No. 2, pp. 11-23.

Popović, D.B. et al., "Neural Prostheses for Walking Restoration", Journal of Automatic Control, University of Belgrade, 2008, vol. 18, No. 2, pp. 63-71.

Stein, R.B. et al., "Surface Electrical Stimulation for Foot Drop: Control Aspects and Walking Performance", Journal of Automatic Control, University of Belgrade, 2008, vol. 18, No. 2, pp. 47-52.

International Search Report issued by the International Searching Authority (ISA/O.E.P.M.) on Feb. 11, 2010 in connection with International Application No. PCT/EP2009/068023.

* cited by examiner

APPARATUS FOR EXTERNAL ACTIVATION OF PARALYZED BODY PARTS BY STIMULATION OF PERIPHERAL NERVES

This application is a §371 national stage application of PCT International Application No. PCT/EP2009/068023, filed Dec. 30, 2009, the contents of all of which are hereby incorporated by reference into this application.

FIELD OF THE INVENTION

The present invention relates to an apparatus for external activation of paralyzed body parts by stimulation of peripheral nerves, in particular by electrostimulation.

BACKGROUND OF THE INVENTION

After an injury or disease of the central nervous system (CNS) parts of the body will be functioning normally, but parts of the body will be paralyzed. Many muscles will be connected to the CNS below the level of injury; thus, they are innervated, but functionally paralyzed (not controllable volitionally). Many sensory pathways are connected to the CNS, yet their function is lost or modified because the information that they carry is not relayed to the corresponding higher centers within CNS.

Functional electrical stimulation (FES) can be considered as a bypass of the impaired sensory-motor mechanisms. FES must provide synergistic actions of many muscles, full control over the each of the muscles by following the findings about the size principle, recruitment order, and recruitment rate, and it should also include sensors feedback for both operation of the system and cognitive awareness of the action if it is to be effective. In parallel, it must be practical to allow independent and effective daily use by a person with disability.

In biological systems the regulation of the strength of a motor response is done through the number of active motor nerve fibers and the rate at which they trigger action potentials: recruitment and temporal summation, respectively. In a physiological contraction, the recruitment order is fixed; slow, fatigue-resistant motor units are active at a lower voluntary effort than larger, fast, fatigable units. The second mechanism affecting the overall force developed by the muscle is temporal summation. The frequency at which the generated muscle forces are sufficiently smooth is known as fusion frequency. The point at which fusion is achieved depends upon the speed of contraction of the activated muscle fibers, and therefore ultimately upon the level of recruitment. In biologically innervated muscles the motor neurons act asynchronously at frequencies that are typically bellow 5 pulses per second; yet, the net effect is a smooth contraction.

In paralyzed muscles electrical stimulation is delivered to innervation pathways to replace the missing biological control signals in bursts of pulses. In an externally induced recruitment, the recruitment order is not known a priori, but depends upon the variables of position and geometry as well as fiber size. An inverse order of electrically induced recruitment is typical when applying FES; the largest fibers are being easily excited, compared with small fibers. This implies that the recruitment has to be considered at all times in order to provide controlled and graded externally induced activation. The recruitment of nerve fibers with increasing stimulus pulse amplitude or duration is nonlinear. For this reason, a linear increase of muscle output force cannot be achieved by a linear change in the input. In externally activated muscles it is impossible with present technology to mimic normal activation, since it is rather difficult to individually activate motor units; hence, the fusion occurs at about 20 pulses per second. Increasing the stimulus frequency above the fusion frequency to the level of tetanus results in a further increase in force. Up to 40 or 50 percent of the maximum muscle force may be regulated by temporal summation from fusion to tetanus.

The force generated by the muscle is directly related to the intensity of stimulation. The intensity of stimulation is directly related to the amount of charge delivered by a pulse. The minimum level of charge is determined by chronaxia, or I-T (amplitude of pulse I vs. pulse duration (width) T). Thereby, the amplitude modulation (AM) or pulse width modulation (PWM) governs the level of recruitment, that is, the force. The recruitment modulation should guaranty reproducibility; therefore consider changes that are likely to occur during prolonged periods of activation. Most, if not all, FES systems activate simultaneously many motor units.

The sensory system in humans operates as an extra large neural network that has been trained through numerous trials and errors. The biological sensory system components provide frequency coded series of binary information, and the process of fusion of this information is not completely understood and described in literature. The inputs that play major role are vision, vestibular system, auditory system, and somatosensory system (exteroception and propriception). Natural control operates in space that is qualitatively described (e.g., hand in contact with an object, elbow fully extended, body erected, etc.). In contrast, artificial sensors systems transform a physical quantity into an useful electrical signal that carries quantitative information about the physical quantities in question. In a highly reduced version of an artificial sensor, the single threshold method applied to the output is a binary signal; hence, if frequency coded it would be a replica of a sensory cell. Somatosensory systems of a human communicate with the brain via the spinal cord, and visual, auditory, and vestibular systems directly. The spinal cord serves both as a relay and as an integration and processing mechanism during the translation of the signal from the periphery to the brain.

In summary, the task for generating functional movement is extremely complex: replacement of a controller that acts on a multi-actuator system based on a multi-sensor system and heuristically optimized rules. From the engineering point of view the system to be controlled is multi input, multi output, time varying highly nonlinear system in which individual parameters can only be estimated based on nonperfect models.

Following elements are known from the prior art (Special issue J Automatic Control, Vol 18(2), 2008):
  Models of electrical field (current density) distribution when electrical stimulation is applied;
  Surface electrodes with adhesive hydrogel in various sizes;
  Textile substrate single pad or multi-pad electrodes in various sizes with hydrogel or made conductive when wet;
  Various garment type alignments for the electrodes;
  Microprocessor based current regulated or voltage regulated multi-channel stimulators suitable for safe application of surface electrical stimulation;
  Electronic stimulators with up to eight channels with numerous predefined stimulation patterns for exercise and limited number of functional movements (grasping, walking);

MEMS and EMG sensors that measure acceleration, position, joint angle, pressure, force, and level of muscle effort;

Model-based controllers that drive the multi-channel stimulator to allow the tracking of predefined trajectories;

Finite-state controllers that operate based on feedback and predefined synergies.

However, there are no practical systems which can be used for therapies of individuals with hemiplegia, multiple sclerosis, cerebral paralysis, incomplete paraplegia, incomplete tetraplegia, tremor, and other movement disorders. The reasons for the lack of these systems are: non sufficiently selective stimulation, fast occurring muscle fatigue, not sufficiently adaptive and robust control algorithms to allow instrumental adaptation to the needs of patients, problems with donning and doffing of the system, and not sufficiently functional in operation.

SUMMARY OF THE INVENTION

The object of the invention is to provide an integrated system for sensor-driven control of paralyzed body members leading to function (e.g. grasping, transferring objects, walking). The present invention provides thus an apparatus for external activation of paralyzed body parts by stimulation of peripherals nerves according to claim 1, which solves the problems of adjusting location and/or stimulus intensity at multiple stimulation points and therefore eases the use of a multichannel electrostimulation system e.g. in an configured array. Advantageous embodiments are defined in the dependent claims.

DETAILED DESCRIPTION OF THE DRAWINGS

To complete the description and in order to provide for a better understanding of the invention, a set of drawings is provided. Said drawings form an integral part of the description and illustrate preferred embodiments of the invention, which should not be interpreted as restricting the scope of the invention, but just as examples of how the invention can be embodied. The drawings comprise the following figures.

DETAILED DESCRIPTION OF THE INVENTION

Figure 1:
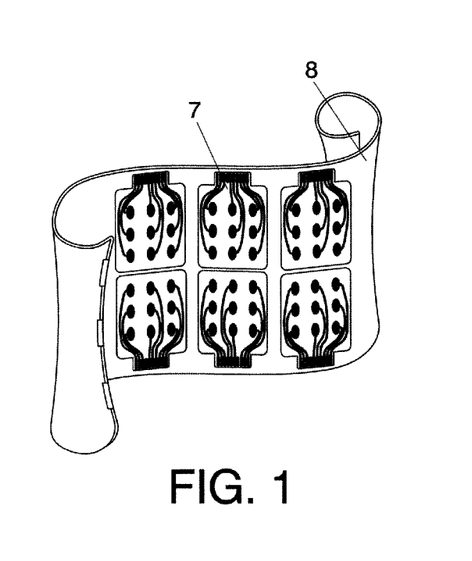
FIG. 1.—soft interface according to the invention integrating the multi-pad electrodes contacting the skin and the back layer comprising controls and stimulation electronics.
Figure 2:
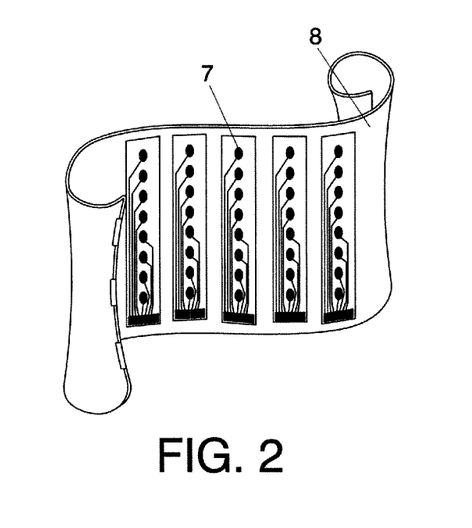
FIG. 2.—soft interface according to the invention integrating the strip multi-pad electrodes contacting the skin and the back layer comprising controls and stimulation electronics.
Figure 3:
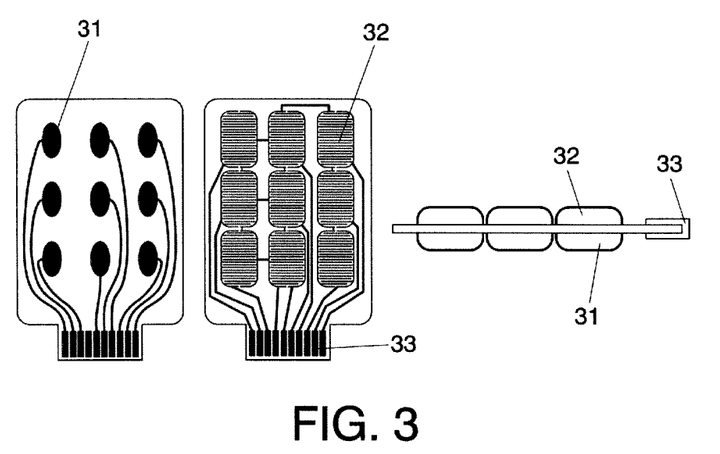
FIG. 3.—multi-pad electrode design with 9 contacts in 3×3 distribution and back layer comprising touch sensitive pads in corresponding positions to set-up stimulation location and intensity.
Figure 4:
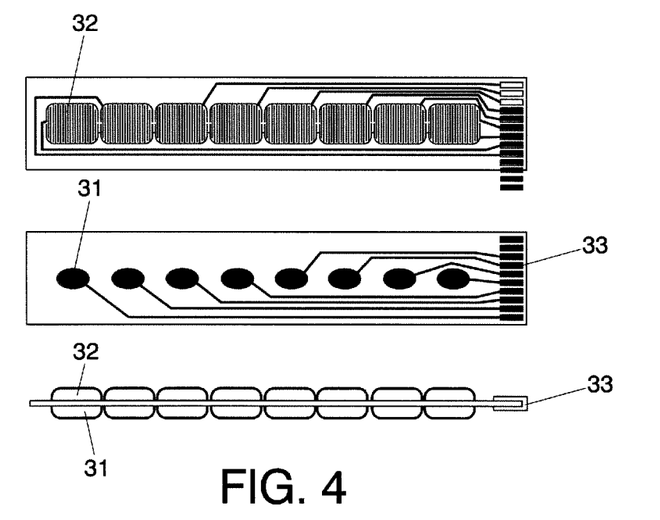
FIG. 4.—multi-pad electrode design with 8 oval contacts in 1×8 distribution and back layer comprising touch sensitive pads in corresponding positions to set-up stimulation location and intensity.

The multi-pad sleeve of the invention is made of soft Neoprene or a similar skin friendly material (8), which integrates the multi-pad electrodes (7) contacting the skin and the back layer comprising controls and stimulation electronics as seen in FIG. 1 and FIG. 2. Multi-pad electrodes are part of the multi-layer interface between the stimulator and the skin, where pads are small enough to allow controlled current flow between the anode and cathode. The location of the cathode (called electrode through this text) on the body determines where muscles or nerves are activated. The anode, can be located at any position of the same body and is often referred as indifferent electrode. Thus, a multi-pad electrode used as cathode can direct the electric current and therefore the activation of peripheral nerves depending on the configuration of the activated pads. Moreover, selective activation allows the application of low frequency activation of motoneurons, which postpones fatigue that is typical for electrical stimulation with surface electrodes with present devices. A multilayer interface can be incorporated to the apparatus to eliminate uneven distribution of stimulation current which is ineffective; yet, unpleasant and sometimes painful. Two preferred multi-pad electrode designs are shown in FIG. 3 and FIG. 4 but arbitrary shape and number of pads could be utilized. The multi-pad electrodes are integrated into the soft and flexible substrate that is designed in a manner which allows positioning of the system in just one possible way; thereby, independent application by the individual with paralysis on his own, or with minimal support of others who are not professional caregivers is made possible.

FIG. 3 and FIG. 4 show the design of two preferred multi-pad multi-layer electrodes of the invention. The stimulation layer (31) consists of an arbitrary number of contacts made in arbitrary various shapes. Two preferred designs have oval contacts distributed in 3×3 or 1×8 matrixes. The size and shape of the pads within the multi-pad electrode is chosen so as to produce comfortable but also selective stimulation. These requests are opposite in terms of pad's size. Bigger pads create lesser current densities during stimulation therefore producing less pain. In contrast, smaller pads create greater current densities followed with pain generation. The invention is provided with a relatively small pad base on top of which conductive gel is positioned. Gel size and shape determines effective electrode area (gel, commonly used conductive hydrogel is with respect to the skin a relatively good conductor; as such the size of the gel will determine the electrode area).

The sensory layer (32) overlaps stimulation layer and has the same shape and number of stimulation adjustment elements as electrodes, adjusting activation and/or intensity;

one sensor per contact. Pressure sensors located in sensory layer allow the control system to determine which contacts need to be active and which inactive. Data obtained by these sensors is available to the controller via connector (33).

Contact switches or capacitive switches could be used instead of pressure sensors. Connectors for the multi-pad electrode are attached to the cable by a clamp.

Figure 5:
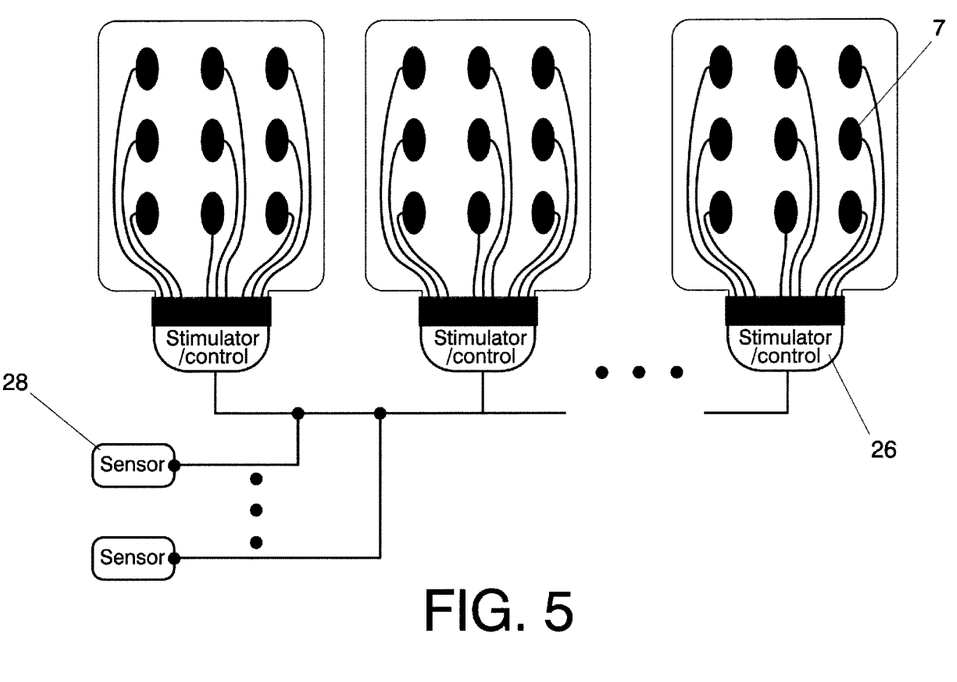
FIG. 5.—sketch of the stimulation layer with smart driver units that are controlled by the built in controller connected with the sensors system for automatic setup and use in real time FIG. 6.—sketch of the multi-array electrodes with the corresponding components.
Figure 6:
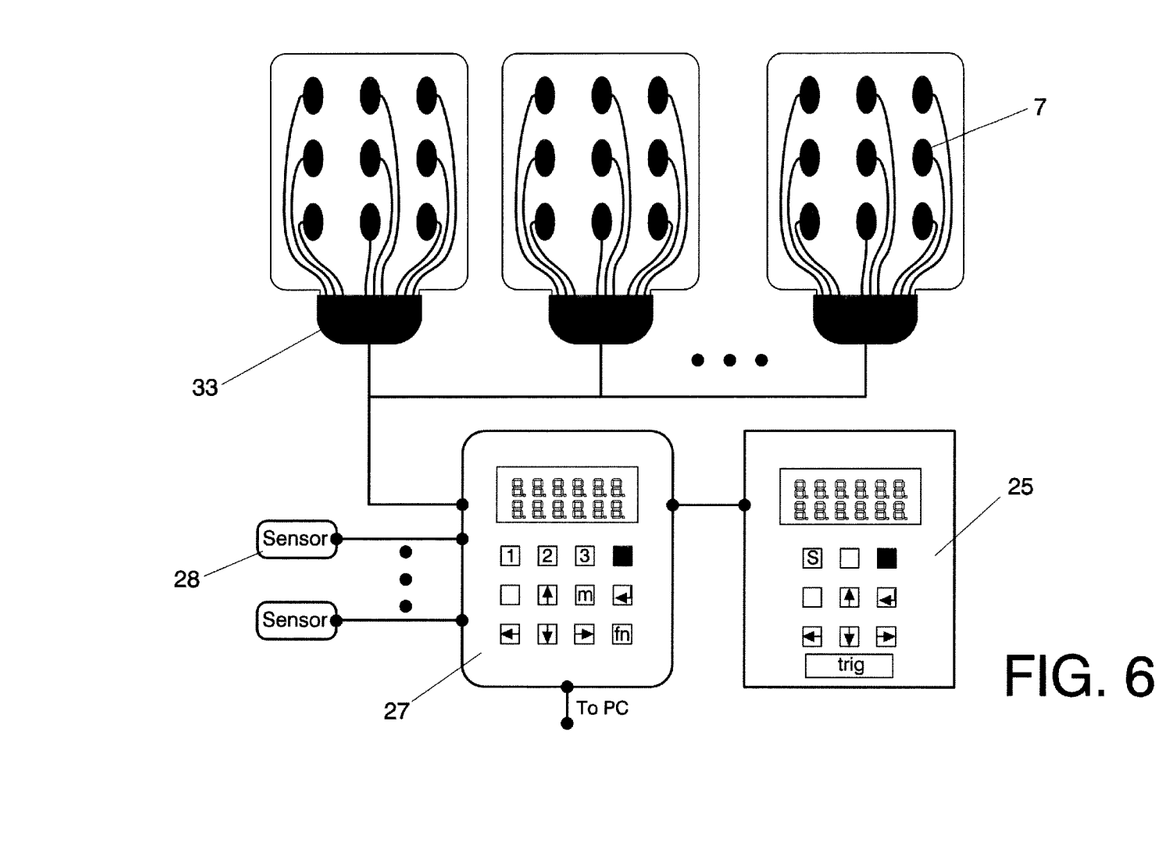
Figure 7:
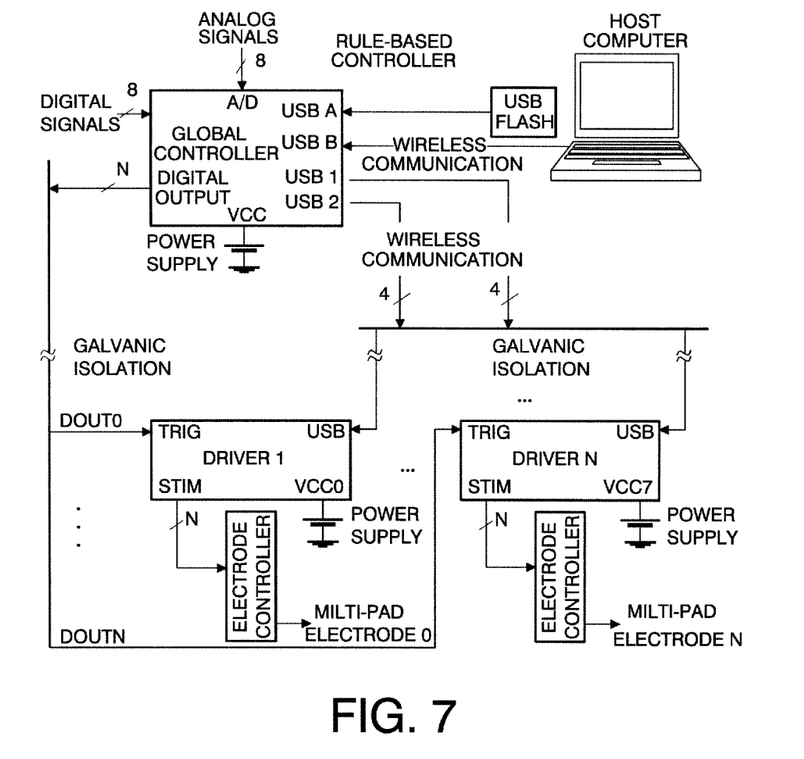
FIG. 7.—overall description of all components of the system.

The back side of the multi-pad electrodes is the support for the smart driver units that are controlled by the built in controller (26) shown in FIG. 5. The controller can utilize an own energy supply made of either disposable or a rechargeable battery or batteries. It implements the so called rule-based control shown in FIG. 7. Rule base control is a finite state method that uses knowledge captured from observations by means of machine intelligence and human heuristics. A possible system configuration with a global controller (27) is shown in FIG. 6. The global controller (27) has a keyboard and a LCD display for user control input. The user can choose a desired mode of operation between several preprogrammed modes. For navigation between different modes and setting operational parameters, keyboard navigation arrows are designated. The global controller can be attached to any number of multi-pad (7) electrodes needed for specific mode of operation. It can also be connected to appropriate external sensors (28) for the desired operation mode. Sensors include inertial MEMS sensors, accelerometers and gyroscopes; length and pressure sensors located in the glove (3); and bend or force sensors in the sensory-layer of the multi-pad electrodes. Communication with all the sensors is conducted through an inertial sensor and controller, ISC (21). The global controller implements rule-base control for the whole system based on sensory inputs (28) and a preferred mode of operation; controlling deployment of the stimulation pulses to optimal contacts of the multi-pad electrode. Optimal contacts are contacts selected by the user through activation response adjustment to achieve a desired contraction or sensory function, e.g. muscle activation of a specific set of muscle fibers or stimulation of sensory nerves to elicit a reflex like the peroneal withdraw reflex. Stimulation pulses are generated in electrode drivers and can be implemented in the controller (26) or/and in the stand-alone electrical stimulator (25). In one realization the predefined stimulation sequence is executed depending on the operation mode. For every operation mode a different stimulation sequence is defined. Every electrode has its own electrode driver, thus making the electrodes electrically isolated from one another. Online adjustments by the global controller can affect amplitude, duration time, frequency and turning on/off of each stimulation channel independently. An example of a stand-alone electrical stimulator (25) has a keyboard and numeric LCD display that allows the user to manually set the stimulation sequence parameters for each mode. The global controller has a communication link with a host computer (PC) for online or offline adjustments of the rule-base control.

The operation of the device has two phases: Setup and Functional use. Switching between these phases is performed by the user as a mode of operation of the controller. The Setup phase considers the use of multiple sensors (some can be temporary contacted to the body or even be contactless, vision based) and a special software that sets the thresholds, and uses an optimization procedure for the selection of the most effective electrode pads for a desired function, as for example hand grasp. The Functional use of the system preferably considers the use of the sensors positioned and integrated in various garments as for example shown in FIG. 9.

Figure 9:
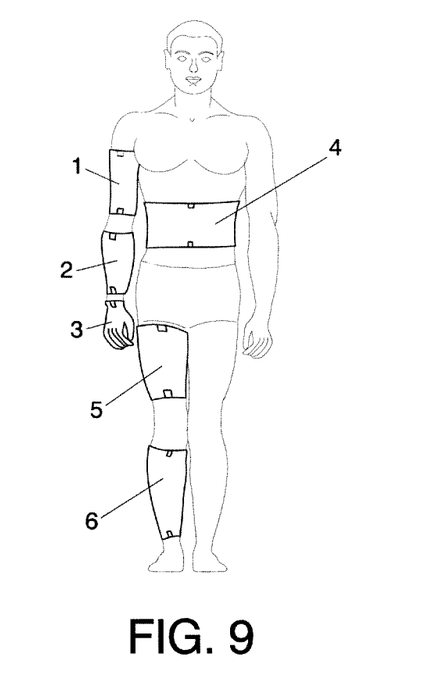
FIG. 9.—general embodiment of the multi-layer intelligent FES.

FIG. 9 shows the different applications of the invention. In the drawing there are different systems shown: a system for control of forearm and partial control of the hand (1), a system for control of the forearm and hand orientation and control of fingers (2), one for control of the trunk (4) and systems for control of upper and lower leg (5),(6).

Figure 8:
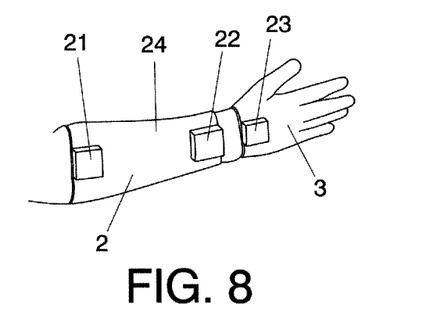
FIG. 8.—embodiment for the forearm in a glove-shape.

FIG. 8 shows the embodiment of a forearm device (2). It comprises a multi-pad sleeve according to the invention (24) and inertial sensors housings with connectors (ISC 21 and 22). The forearm system (2) is made of Neoprene or similar skin friendly material, and its adjustable diameter allows it to be fitted on any forearm. Inertial sensor housings with connectors (21) are located at both ends of the forearm system. Each ISC module consists of MEMS inertial sensors, a battery power supply and connectors. MEMS inertial sensors, accelerometers (22) and gyroscopes (23) are utilized for obtaining body parts spatial orientation by the controller. The sensors integrated into the system operate as a network and provide qualitative information about the functional status of the body members; thus providing information about the functionality and command signal for the movements to reproduce the desired movement. Sensory signal conditioning and processing circuitry is also located in the ISC. The power supply can be located in any ISC and consists of one or more batteries. Batteries could be rechargeable or disposable. Charging of batteries is conducted through the connector of an ISC by an external charger. If the global controller (27) is in use, it provides battery power supply for all units. The global controller has multiple functions: it supervises and powers all units, synchronizes and facilitates communication between multiple systems and allows recharging of the batteries. The global controller is connected to a PC by means of a cable or a wireless interface.

A finger flexion/extension and hand position (pronation/suppination as well as radiaVulnar deviation) measurement glove (3) is part of the system designed for use mainly during Setup phase, and in some modes of operation in Functional phase if a forearm system is used. The glove consists of multiple sensors: MEMS inertial sensors, length sensors and pressure sensors. The pressure sensors measure when the fingers are in contact with an object the grasp force. The rule-based controller defines rules for hand functionality using these sensory inputs. The glove also has a ISC unit (23)

A functional use of the electrode as for example in a hand grasp orthosis consist of a sequence of different grasp configurations (configurations of the hand and fingers), which will be set up with the claimed electrode (using the touch sensors). In the Functional mode these setups will be selected depending of the hand orientation, position and configuration using a rule based controller.

Figure 10:
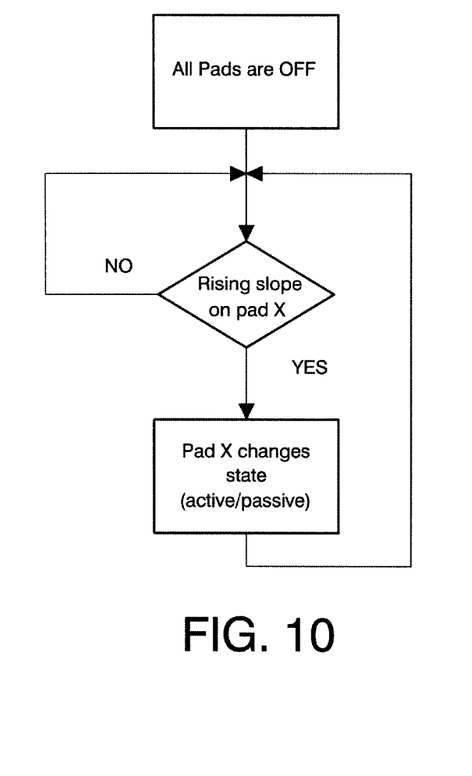
FIG. 10.—flowchart showing an activation control procedure.

Operation mode 1 provides activation control of individual pads based on sensory layer data. This feature is available in both Setup and Functional phase. The main functional principle of mode 1 is to select/command the distribution of stimulation pulses to desired pads in an on/off manner. A protocol for controlling active field (fields) is guided by the pressure applied on the sensory layer. When a rising slope on a stimulation adjustment element (sensor) is detected, the stimulation pad underneath changes state, if active it becomes inactive and vice versa. The control algorithm is shown in (FIG. 10). The stimulation amplitude is set indirectly on the control unit input interface.

Figure 11:
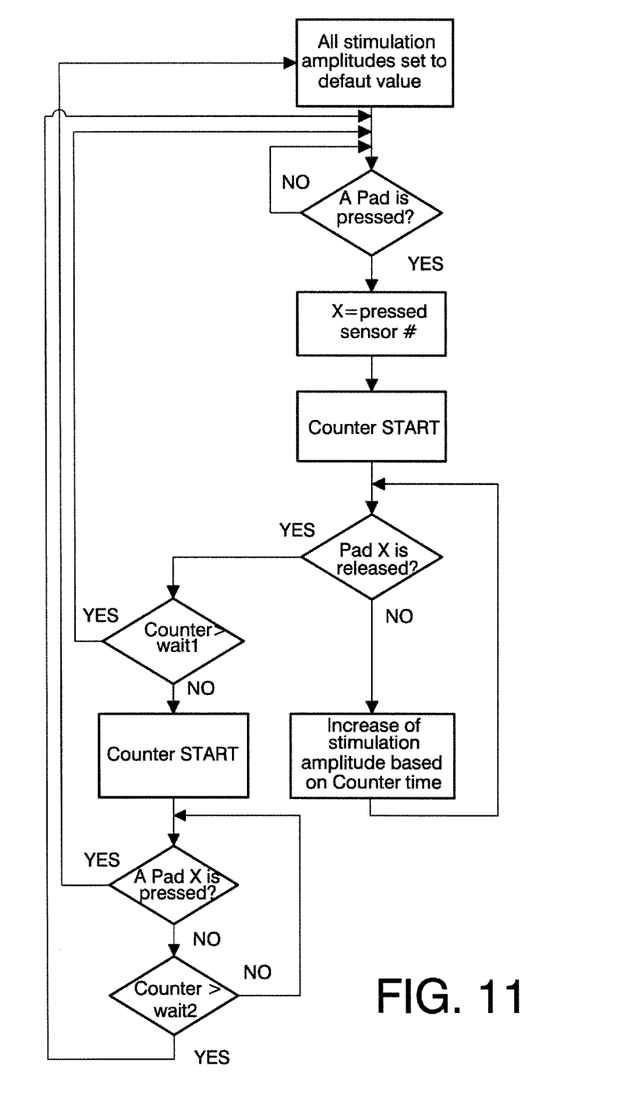
FIG. 11.—flowchart showing an amplitude adjustments procedure.

Mode 2 incorporates stimulation pulses amplitude adjustments. This feature is available in both the Setup and Functional phase. During the Setup phase the user performs adjustments of stimulation pulses amplitude for all pads that need to be activated. The pulse amplitude will be adjusted by the user according to the specific need that can be selectivity, comfort, motor or sensory threshold or performance. The control procedure is shown in FIG. 11. Default stimulation amplitudes in Setup phase are 0. an increase of the stimulation amplitude is determined by the duration of sensor pressing. Values set by user are stored in memory in order to be used in Functional phase as the default values.

Figure 12:
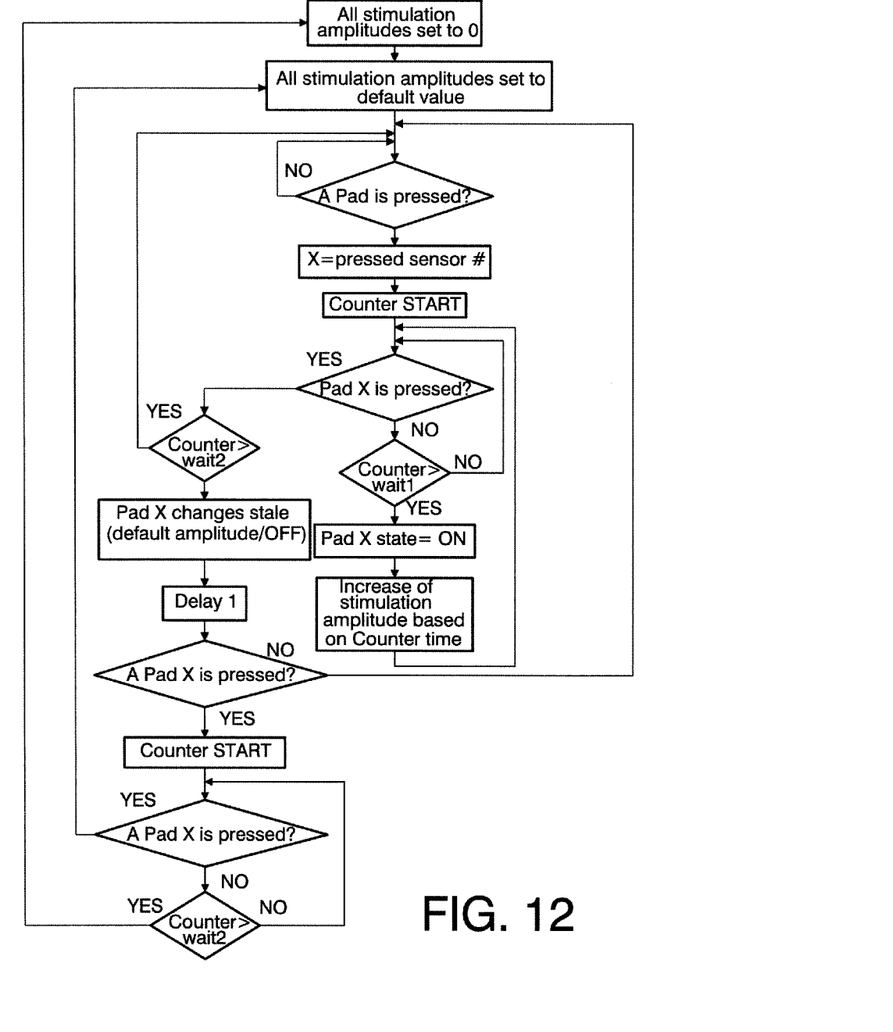
FIG. 12.—flowchart showing an activation/amplitude adjustments control procedure.

Mode 3 allows both activation and amplitude adjusting functions. FIG. 12 Shows control algorithm for embodiment 4.

In mode 4 a processing and storage unit is used which allows to store multiple setups made in the manner as described in the previous embodiments. These setups e.g. which pads should be active as determined using the procedure in FIG. 11 can be timely sequenced in the Functional phase. As such different pad setups can be used more complex functional tasks e.g. a setup that stimulates muscles to actuate finger extension followed by another pad setup that stimulates wrist extension muscles, which are anatomically located more proximal than the finger extensors. Timing to change between different setups can be adjusted by a program deterministically or using processed sensor information that records user activities e.g. limb movements or limb configurations or any other kind of artificial or natural sensor. The transition from one to the other setup can be either abrupt or smooth. A smooth transition calculates pad setups that are in-between like it is done when morphing between two images. A multiple number of multi-pad electrodes can be coordinated using this concept of setups with the timing and transition coordination. A typical application is to use two or three such multi-pad electrodes for the stimulation of finger and hand function for hand grasp and release, or 4-6 pads to stimulate foot and leg movements for locomotion.

Figure 13:
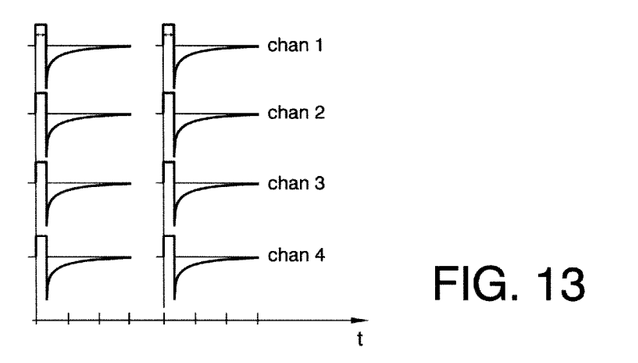
FIG. 13.—graph of the synchronous stimulation.

Multi-pad electrode FES could be implemented by synchronous or asynchronous stimulation of the active pads. Synchronous stimulation results in superposition of the electrical currents applied through active pads (FIG. 13). The resulting field may produce excitation of nerves which are below threshold when stimulated by each field separately. Mode 5 includes synchronous stimulation of pads during Setup and Functional phase. This way, more degrees of freedom for stimulation parameters are introduced when stimulating with spatially fixed multi-pad electrode.

Figure 14:
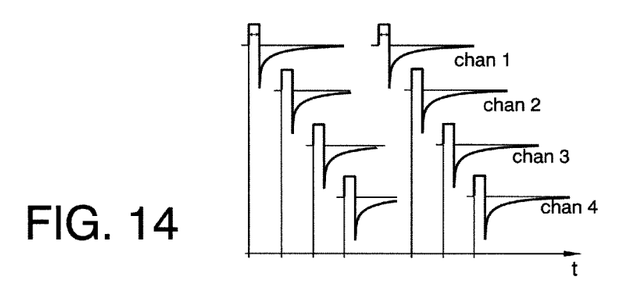
FIG. 14.—graph of the asynchronous stimulation.

Asynchronous stimulation relays on sending stimulation pulses to pads within the multi-pad electrode sequentially, by delaying one stimulation pulse after another in a short time (FIG. 14). Mode 6 includes asynchronous stimulation of pads during Setup and Functional phase. When stimulated asynchronously a stimulation pulse is switched to only one pad, such that the excitation of nerves, is uniquely determined for each pulse and not determined by impedance distribution between multiple pads and the indifferent electrode. It allows better reproducibility of stimulation parameters.

Figure 15:
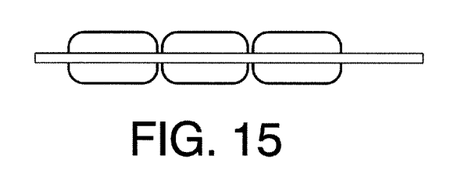
FIG. 15.—single substrate multi-pad electrode.

An alternative embodiment of a double-layer multi-pad electrode is designed as a single substrate layer with stimulation and sensory layers on its sides and shown in FIG. 15.

Figure 16:
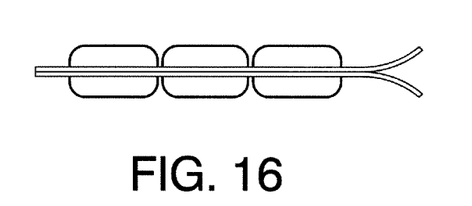
FIG. 16.—double substrate multi-pad electrode.

Another embodiment of a double-layer multi-pad electrode is designed as two separate substrate layers, one carrying stimulation pads and second carrying stimulation adjustment elements (FIG. 16).

Figure 17:
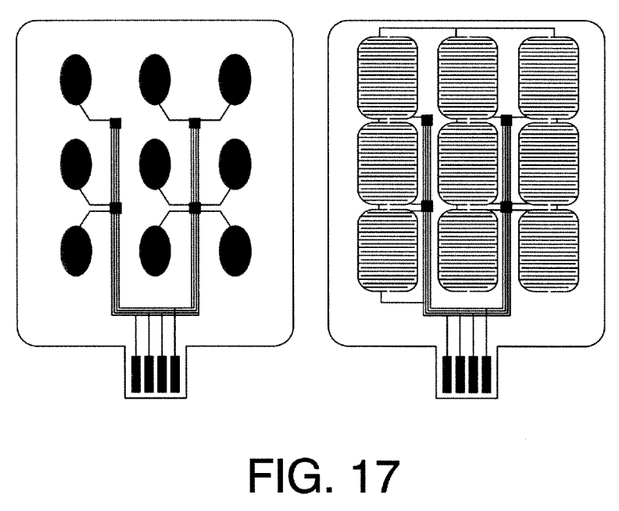
FIG. 17.—ASIC Multi-pad electrode module.

FIG. 17 shows an embodiment of a multi-pad electrode comprising ASIC stimulators with controllers (application specific integrated circuits). The functions of switching on/off of the stimulation and the setting of the stimulation intensities for each pad are integrated in an ASIC placed on the electrode substrate. One ASIC is responsible of, for example, 4 pads and has as input a high supply voltage and a control signal. Such an embodiment solves the problem of complex wire routing, specifically when the multi-pad electrode consists of many pads. In the configuration that one ASIC comprises integrated analog and digital circuits for four electrodes and sensor pads, the multi-channel electrode can be of any size without increased complexity of the wiring as all ASIC's are supplied and controlled with the same signal lines. ASIC modules provide full functionality for modes 1-9. FIG. 17 shows 4 connections shared by all ASIC modules, 2 high voltage source wires e.g. 150 V and 2 communication wires with the information about stimulation channel switching, channel synchronization, stimulation amplitudes and pulse durations. Alternatively, ASIC modules can be wired using only 2 connection lines providing high voltage with superimposed communication signals.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiments described herein, but also encompasses any variations that may be considered by any person skilled in the art (for example, as regards the choice of materials, dimensions, components, configuration, etc.), within the general scope of the invention as defined in the claims.

The invention claimed is:

1. An apparatus for external activation of paralyzed body parts by electrical stimulation of peripheral nerves or muscles delivered by electrodes, which comprises a soft apparel (8) comprising on one side (31) a layer provided with multi-pad electrodes, said layer being configured to contact the skin of the user during use of the apparatus, and on the opposite side (32) a layer comprising activators, wherein each activator is adapted to activate and control each electrical pulse delivered to a corresponding multi-pad electrode separately, wherein each activator is associated to a single electrode, wherein each multi-pad electrode overlaps a corresponding activator, the material of the apparel being there between, the activators being pressure driven sensors, said pressure driven sensors being used for determining which electrodes need to be active and which inactive, said apparatus further comprising a controller means adapted to control said activators by adjusting activation, deactivation and intensity of an electrical pulse delivered to each electrode individually, in reply to corresponding individual data obtained by said pressure driven sensors, said individual data being a rising slope indicative of the pressure applied on a pressure driven sensor and a time duration indicative of the duration of pressure applied on a pressure driven sensor.

2. The apparatus according to claim 1 further comprising movement and/or position sensors (22) connected to the controller.

3. The apparatus of claim 2 wherein the sensors are independently force sensors, accelerometers, inertial sensors, gyroscopes, or length or bend sensors.

4. The apparatus according to claim 1 further comprising movement and/or position sensors (22) connected to the controller.

5. The apparatus according to claim 4, further comprising at least one ASIC on the electrode substrate layer carrying stimulation pads (31) and wherein the multi-pad electrodes are grouped, the ASIC being adapted to control the voltage and/or amplitude delivered to the group.

6. The apparatus according to claim 1 wherein the controller is adapted to be connected to a personal computer.

7. The apparatus according to claim 1, further comprising at least one ASIC on the electrode substrate layer carrying stimulation pads (31) and wherein the multi-pad electrodes are grouped, the ASIC being adapted to control the voltage and/or amplitude delivered to the group.

* * * * *